US00PP19874P2

(12) United States Plant Patent
Carruth

(10) Patent No.: US PP19,874 P2
(45) Date of Patent: Mar. 31, 2009

(54) POLYANTHA ROSE PLANT NAMED 'WEKAIRYVEN'

(50) Latin Name: *Rosa hybrida*
Varietal Denomination: WEKairyven

(75) Inventor: Thomas F. Carruth, Altadena, CA (US)

(73) Assignee: Weeks Wholesale Rose Grower, Inc, Pomona, CA (US)

( * ) Notice: Subject to any disclaimer, the term of this patent is extended or adjusted under 35 U.S.C. 154(b) by 0 days.

(21) Appl. No.: 11/985,379

(22) Filed: Nov. 14, 2007

(51) Int. Cl.
*A01H 5/00* (2006.01)

(52) U.S. Cl. ..... Plt./151
(58) Field of Classification Search ..... Plt./151, Plt./150
See application file for complete search history.

(56) References Cited

PUBLICATIONS http://web.archive.org/web/20061028173913/http://www.edmundsroses.com/cgi–bin/browse.cgi?cat=52&item=381.*

* cited by examiner

*Primary Examiner*—Annertte H Para
*Assistant Examiner*—S. B. McCormick Ewoldt

(57) ABSTRACT

A new variety of Polyantha rose suitable for garden decoration, having flowers of brilliant scarlet coloration.

1 Drawing Sheet

Classification:
The present invention relates to a new *Rosa hybrida* plant.
Variety denomination:
The new plant has the varietal denomination 'WEKairyven'.

BACKGROUND OF THE INVENTION

This invention relates to a new and distinct variety of Polyantha Rose. It has as its seed parent the variety known as 'MORredfar' (U.S. Plant Pat. No. 10,150) and as its pollen parent the variety known as 'FRYtrooper' (U.S. Plant Pat. No. 9,211).

SUMMARY OF THE INVENTION

Among the features which distinguish the new variety from other presently available and commercial rose cultivars known to the inventor are the following combinations of characteristics: its many hairs on the peduncle and on the receptacle, its long lived flowers, its brilliant scarlet coloration that last throughout the life of the flower and its many flowered clusters. The plant has a bushy spreading growing habit, suitable for outdoor garden decoration.

Asexual reproduction of the new variety by budding as performed in Kern County and Pomona, Calif. shows that the foregoing and other distinguishing characteristics come true to form and are established and transmitted through succeeding asexual propagations. 'WEKairyven' may be asexually propagated by cuttings, budding and grafting. The budding and grafting successfully occurred on the plant/rootstock *Rosa hybrida* cv. 'Dr. Huey' (not patented).

Comparison with Parents

The new rose may be distinguished from its seed parent, 'MORredfar' by the following combination of characteristics: whereas 'WEKairyven' bears semi-double flowers (about 6 to 9 petals) of brilliant scarlet coloration, 'MORredfar' bears double flowers with significantly heavier petalage (about 20 to 30 petals) of red coloration. The new variety has a bushy moderately spreading medium height growing habit (about 75 to about 90 cm. in height), whereas the seed parent has a ground cover type significantly shorter growing habit.

The new variety may be distinguished from its pollen parent, 'FRYtrooper' by the following combination of characteristics: whereas 'WEKairyven' bears semi-double flowers (about 6 to 9 petals) of brilliant scarlet coloration, 'FRYtrooper' bears double flowers with significantly heavier petalage (about 18 to 22 petals) of clear red coloration. The new variety bears small flowers (about 2.4 to about 3.9 cm. in diameter), whereas the pollen parent bears significantly larger flowers (about 4 to about 6 cm. in diameter).

Comparison with the Closest Commercially Available Cultivar

The new variety may be distinguished from its closest commercially available cultivar, 'KORtemma' (U.S. Plant Pat. No. 9,115) by the following combination of characteristics: whereas 'WEKairyven' bears semi-double flowers (about 6 to 9 petals) of brilliant scarlet coloration, 'KORtemma' bears double flowers with significantly heavier petalage (about 20 petals) of bright red coloration. The new variety usually bears its flowers in clusters of as few as 4 to as many as 54 or more per stem, whereas the closest commercially available cultivar bears clusters of significantly lesser flowers (about 3 to 7 per stem).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966)

except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

Flower:

The new variety usually bears its flowers in clusters of as few as 4 to as many as 54 or more per stem. Flowers are borne in regular rounded to somewhat pyramidal clusters on strong short to medium length stems (about 18 to about 72 cm.). Outdoors, the plant blooms abundantly and nearly continuously during the growing season. The flowers have no fragrance.

Bud:

The peduncle is about 1.3 to about 3.2 cm. in length, of slender caliper (about 0.1 to about 0.15 cm. in diameter), and usually erect. It is moderately smooth, with few stipitate glands and many hairs. Peduncle color is between 146C and 146B often moderately suffused, especially on the side exposed to the sun, with between 183B and 183C.

Before the calyx breaks, the bud is about 0.6 to about 1.0 cm. in diameter at the widest point, about 0.9 to about 1.3 cm. in length, and pointed in shape. The surface of the bud bears few foliaceous appendages, some hairs and few stipitate glands, usually with slender entire foliaceous parts extending beyond the tip of the bud about ½ or more of its length. Bud color is between 146A and 146C sometimes lightly suffused, especially on the side exposed to the sun, with between 187B and 183B.

The sepals are about 1.5 to about 2.1 cm. in length and about 0.4 to about 0.6 cm. in width at the widest point. The outer surface color of the sepal is between 146A and 146C sometimes lightly suffused, especially on the side exposed to the sun, with between 187B and 183B. The inner surface color of the sepal is between 137A and 139C. After the sepals open, the inner surface color is sometimes ligthly suffused, especially on the area exposed to the sun, with near 187B. The sepals are covered with fine wooly tomentum; sepal margins are lined with many hairs.

The receptacle of the flower is of medium length (about 0.3 to about 0.5 cm.) and somewhat thin in caliper (about 0.4 to about 0.5 cm. in diameter). The receptacle is rounded in form. Its surface is very smooth with many hairs and with thick fleshy walls. The receptacle color is between 137C and 146C sometimes lightly suffused, especially on the side exposed to the sun, with between 187B and 183B.

As the petals open (after the calyx breaks), the bud is about 0.7 to about 1.1 cm. in diameter at the widest point, about 1.1 to about 1.4 cm. in length, and ovoid in form. The color of the under surfaces of the newly opened petals is between 53A and 46A. At the point where the petal attaches, there is a small zone of between 1C and 2C. The color at the base of the upper surfaces of the newly opened petals is between 45B and 46B gradually suffusing toward the edge of the petals with between 53A and 46A. At the point where the petal attaches, there is a small zone of between 4A and 5C.

Bloom:

When fully open, the bloom ranges from about 2.4 to about 3.9 cm. in diameter. Petalage is semi-double with about 6 to 9 petals and about 6 to 9 petaloids irregularly arranged. When partially open, the bloom form is moderately globular to cupped, and the petals are loosely cupped with petal edges slightly reflexed outward. When fully open, the bloom form is cupped, and the petals are loosely cupped to sometimes somewhat folded laterally with petal edges somewhat reflexed outward.

Petals:

The substance of the petals is moderately heavy and of medium thickness, with upper surfaces moderately satiny to somewhat velvety and under surfaces slightly shiny to almost matte. The petals are about 1.3 to about 1.6 cm. in length and about 1.1 to about 1.6 cm. in width at the widest point. Petal margins are entire.

The outer petals are moderately obovate in shape with rounded apices.

The inner petals are obovate to somewhat oblanceolate in shape with rounded apices.

Petaloids are about 0.8 to about 1.5 cm. in length and about 0.5 to about 0.9 cm. in width at the widest point. Petaloids are irregularly shaped somewhat oblanceolate to subulate with rounded apices.

Newly opened flower:

The under surface color of the outer, intermediate and inner petals is between 53A and 46A. At the point where the petal attaches, there is a small zone of between 2C and 3D. The color at the base of the upper surface of the outer, intermediate and inner petals is between 45B and 46B gradually suffusing toward the edge of the petals with between 53A and 46A. At the point where the petal attaches, there is a small zone of between 6C and 5C.

The under and upper surface color of the petaloids are similar in coloration to the upper and under surfaces of the intermediate and inner petals.

The general tonality of the newly opened flower is between 45B and 46B at the base of the petal gradually suffusing toward the edge of the petals with between 53A and 46A.

Three-day-old flower:

The under surface color of the outer, intermediate and inner petals is between 53A and 46A. At the point where the petal attaches, there is a small zone of between 155A and 155C. The color at the base of the upper surface of the outer, intermediate and inner petals is near 61C that gradually suffuses toward the center of the petal to between 46C and 46B, suffusing toward the edge of the petals with between 53A and 46A and sometimes moderately blushed with as dark as between 187A and 187B. At the point where the petal attaches, there is a small zone of between 4D and 155A.

The under and upper surface color of the petaloids are similar in coloration to the upper and under surfaces of the intermediate and inner petals.

The general tonality of the three-day-old flower is near 61C at the base of the petal that gradually suffuses toward the center of the petal to between 46C and 46B, suffusing toward the edge of the petals with between 53A and 46A and sometimes moderately blushed with as dark as between 187A and 187B.

On the spent bloom, the petals usually persist, fading to between 47B and 46C sometimes moderately blushed with near 53A to as dark as 187A.

In October in Pomona, Calif., blooms on the bush growing outdoors generally last about four to five days. Cut roses from plants grown outdoors and kept at normal indoor living temperatures generally last about four to five days.

Male reproductive organs:

Stamens are average in number (average about 75) and are arranged regularly about the pistils; a few are mixed with petaloids. The filaments are of somewhat short length (about 0.4 to about 0.6 cm.) most with anthers. Filaments are between 4A and 6C in color. The anthers are moderately small for the class and all open approximately at the same time. Anther color when immature is near 22A on the external part and near 10C on the internal part. Anther color at maturity is near 162D on the external part and near 202A on the internal part. Pollen is sparse near 18C in color.

Female reproductive organs:

Pistils vary in number (average about 25). The styles are very even, moderately short in length (about 0.3 to about 0.4 cm.), thin in caliper, and moderately loosely bunched. Stigma color is between 154C and 1C. Style color is between 149D and 145D sometimes lightly suffused with near 53D. Ovaries are usually all enclosed in the calyx.

Hips have not been observed on this variety when grown in Pomona, Calif.

Foliage:

The compound leaves are usually comprised of three to seven leaflets and are borne abundantly. The seven-leaflet leaves are about 7.0 to about 10.9 cm. in length and about 3.8 to about 6.7 cm. in width at the widest point, moderately thin to somewhat leathery in texture, and moderately glossy in finish on the upper surface and matte in finish on the under surface. The terminal leaflets are about 2.4 to about 4.1 cm. in length and about 1.3 to about 2.3 cm. in width at the widest point, shaped oval with acute apices and moderately rounded to somewhat acute bases. Their margins are usually simply serrate.

The upper surface color of the mature leaf is between 139A and 141A. The under surface color of the mature leaf is between 137B and 141A. The upper surface color of the young leaf is between 137B and 146C, sometimes lightly suffused, especially toward the edge of the leaf, with between 187B and 183B. The under surface color of the young leaf is between 147B and 137C, sometimes moderately suffused with between 187B and 183B.

The rachis is somewhat light in caliper and moderately rough. The upper side is deeply grooved with few hairs and stipitate glands on the edges of the grooves. The under side of the rachis is moderately rough with few stipitate glands and small prickles. The rachis color is near 138B on the under side and near 137A on the upper side often suffused on the young leaf with between 187B and 183B.

The stipules are about 0.9 to about 1.6 cm. in length and of medium width (about 0.4 to about 0.5 cm.) with moderately long straight points that usually turn out at an angle of more than 45 degrees. The stipules color is between 137A and 137B often suffused especially on the young leaf with between 187B and 187D.

The petiole is somewhat light in caliper and moderately rough. The upper side is deeply grooved with few hairs and stipitate glands on the edges of the grooves. The under side of the petiole is moderately rough with few stipitate glands and small prickles. The petiole is about 0.5 to about 1.1 cm. in length and about 0.1 to about 0.15 cm in diameter at the widest point. The petiole color is near 138B on the under side and near 137A on the upper side often suffused on the young leaf with between 187B and 183B.

The plant displays an above average degree of resistance to powdery mildew and rust as compared to other commercial varieties grown under comparable conditions in Pomona, Calif. The plant's winter hardiness and drought/heat tolerance are yet to be determined.

Growth:

The plant has a bushy moderately spreading medium height growing habit (about 75 to about 90 cm. in height and about 65 to about 85 cm. spread at the widest point), with full branching. It displays moderately vigorous growth and the canes are of somewhat light caliper for the class (about 0.4 to about 1.0 cm. in diameter at their widest point).

The color of the major stems is between 148A and 147A. They bear some large prickles that are about 0.5 to about 0.8 cm. in length. The large prickles are moderately angled downward to sometimes slightly hooked with a long narrow oval base; prickle color is between 199B and 177C. The major stem bears no small prickles.

The color of the branches is between 137C and 146A sometimes moderately suffused with between 187B and 183B. They bear some large prickles which are of similar size and shape to the large prickles on the major stems; prickle color is between 177B and 166B. The branches bear no small prickles.

The color of the new shoots is between 146A and 146C often moderately suffused with between 187B and 183B. They bear some large prickles which are of similar size and shape to the large prickles on the major stems; prickle color is between 187B and 187C. The shoots bear no small prickles.

I claim:

1. A new and distinct Polyantha rose plant of the variety substantially as described and illustrated herein.

* * * * *

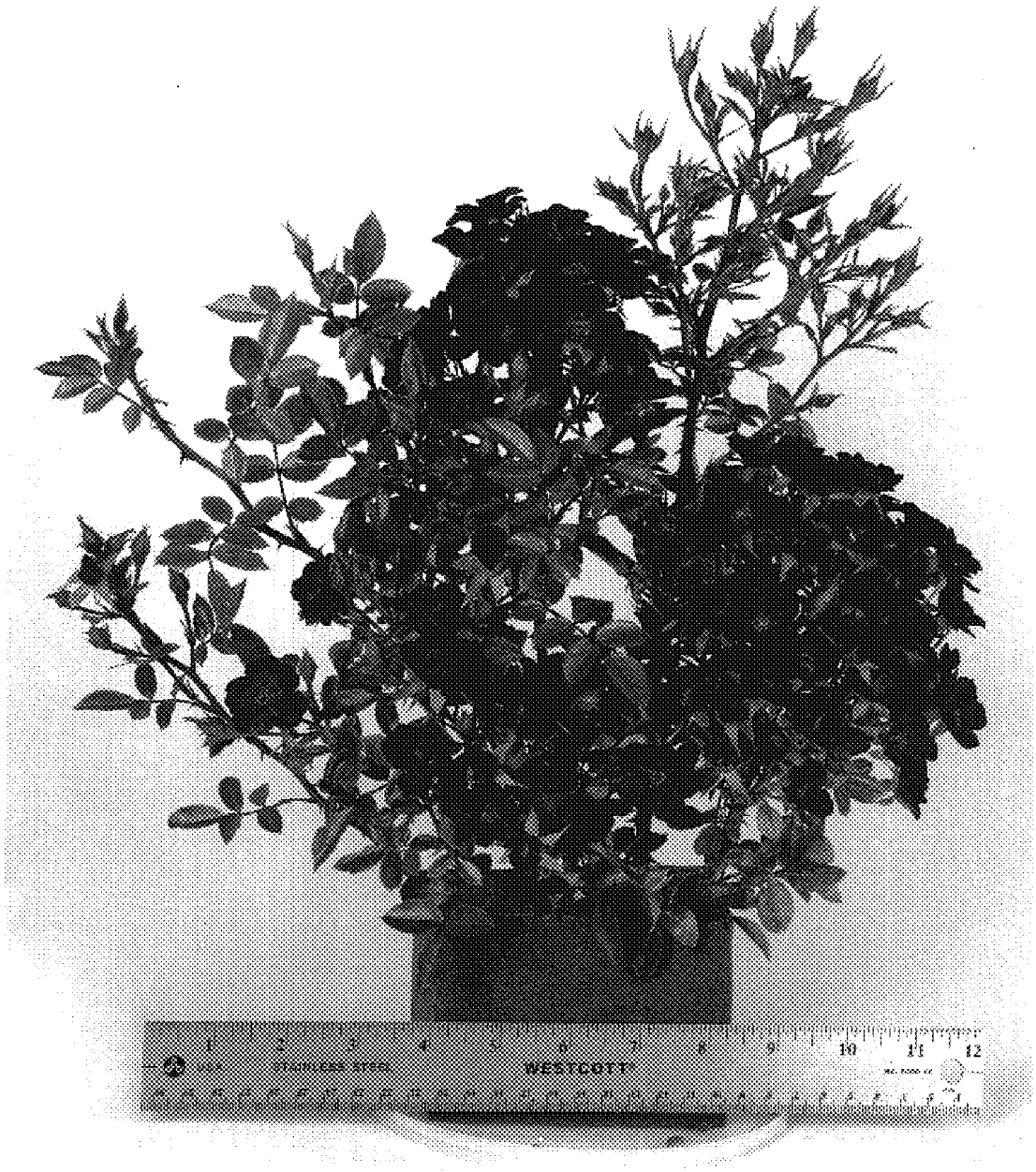
WESTCOTT